United States Patent [19]

Harris

[11] 4,200,104
[45] Apr. 29, 1980

[54] CONTACT AREA MEASUREMENT APPARATUS FOR USE IN ELECTROSURGERY

[75] Inventor: Frank W. Harris, Boulder, Colo.

[73] Assignee: Valleylab, Inc., Boulder, Colo.

[21] Appl. No.: 852,431

[22] Filed: Nov. 17, 1977

[51] Int. Cl.² .................. A61B 17/36; A61N 3/00
[52] U.S. Cl. ..................... 128/303.14; 128/783; 361/42
[58] Field of Search ............. 128/303.13, 303.14, 128/303.15, 303.16, 303.17, 303.18, 2.1 P, 2.1 Z, 404, 413, 416, 417, 418; 361/42

[56] References Cited

U.S. PATENT DOCUMENTS

| | | | |
|---|---|---|---|
| 3,683,923 | 8/1972 | Anderson | 128/303.14 |
| 3,848,600 | 11/1974 | Patrick, Jr. et al. | 128/303.13 |
| 3,901,216 | 8/1975 | Felger | 128/2.1 Z |
| 3,913,583 | 10/1975 | Bross | 128/303.14 |
| 3,923,063 | 12/1975 | Andrews et al. | 128/303.14 |
| 3,933,157 | 1/1976 | Bjorwill et al. | 128/303.14 |

FOREIGN PATENT DOCUMENTS 1139927 11/1962 Fed. Rep. of Germany ...... 128/303.13
1149832 6/1963 Fed. Rep. of Germany ...... 128/303.13

Primary Examiner—Lee S. Cohen
Attorney, Agent, or Firm—Gerald J. Ferguson, Jr.; Joseph J. Baker

[57] ABSTRACT

Patient contact area measurement method and apparatus including a first electroconductive contact element adapted for contact with the patient; a second electroconductive contact element separated from the first contact element and also adapted for contact with the patient; and measuring circuitry disposed between the first and second electroconductive contact elements for measuring the area of contact of the patient with respect to the contact elements. The electroconductive contact elements may comprise (a) each electrode of a split electrosurgical patient electrode, (b) the active and patient electrodes employed in electrosurgery or (c) a cryosurgical probe together with a monitor electrode adapted for contact with the patient.

15 Claims, 9 Drawing Figures

CONTACT AREA MEASUREMENT APPARATUS FOR USE IN ELECTROSURGERY

BACKGROUND AND SUMMARY OF THE INVENTION

This invention relates to an improved method and apparatus for measuring the contact area of one or more electrosurgical electrodes or a cryosurgical probe with respect to a patient's tissue.

In monopolar electrosurgical systems, it is well known to effect cutting, fulguration or desiccation by employing an active electrode having a relatively small cross-sectional area whereby the current density at the treated area is sufficiently high to effect the desired treatment. Assuming the current density is sufficiently high, desiccation occurs if the active electrode is in ohmic contact with the tissue. Assuming the voltage is sufficiently high, cutting or fulguration occurs depending on the type of waveform if the active electrode is in arcing contact with the tissue. A large patient electrode is also normally employed in monopolar electrosurgery to return the current to the electrosurgical generator, the surface area of this electrode being large enough to reduce the current density threat to a point where the possibility of a patient burn is minimal.

There is a possibility the patient may not be in contact with the patient electrode or that a discontinuity may arise in the return circuit from the patient electrode to the generator. If a small grounded object is in contact with the patient at this time, the current from the active electrode will return to the generator through an alternate return path including the small grounded contact point whereby the possibility of a patient burn at the contact points exists. Circuits are known for detecting alternate return ground currents of the foregoing type and effecting appropriate remedial procedures whenever the alternate return current exceeds a predetermined minimum, see for example, U.S. Pat. No. 3,683,923.

Another potential danger exists in that the patient may only be in partial contact with the patient electrode due, for example, to a misapplication of the electrode. The remaining area of contact may be of insufficient size to sufficiently reduce the current density at the return electrode to prevent burning of the patient threat. Safety circuitry is known whereby split (or double) patient electrodes are employed and a DC current (see German Pat. No. 1,139,927, published Nov. 22, 1962) or an AC current (see U.S. Pat. No. 3,933,157) is passed between the split electrodes to sense the contact resistance or impedance between the patient and the electrodes. U.S. Pat. No. 3,913,583 discloses circuitry for reducing the current passing through the patient depending upon the area of contact of the patient with a solid, patient plate, there being employed a saturable reactor in the output circuit, the impedance of which varies depending upon the sensed impedance of the contact area.

It is a primary object of this invention to provide a method and apparatus for detecting a partial loss of patient contact with a split patient electrode using capacitance measuring circuitry where the remaining area of contact is insufficient to reduce the current density at the split patient electrode to a non-dangerous level.

It is a further object of this invention to provide a power supply for contact area measurement circuitry which is isolated from ground to thereby avoid any undesirable effect on the area measurement due to grounding of the patient.

It is a further object of this invention to provide contact area measurement circuitry which operates at an amplitude which is low enough to avoid neuromuscular stimulation and interference with ECG patient monitors.

It is a further object of this invention to provide an improved method and apparatus for measuring the contact area of an active electrode with respect to a patient.

It is a further object of this invention to utilize a split capacitive electrode in conjunction with the cable connecting the split patient electrode to the generator so that the inductive impedance of the cable and the capacitive impedance of the electrode tend to cancel one another out thereby maintaining a low radio-frequency potential on the patient, the frequency of operation being such that the aforesaid effect occurs over a substantially wide range of area of patient contact with the patient electrode.

It is a further object of this invention to provide an inductance in series with the patient return cable to effect a low operating potential on the patient at predetermined frequencies of operation.

It is a further object of this invention to provide circuitry for detecting the contacting of the aforesaid insulated split electrodes with a metal surface.

DETAILED DESCRIPTION OF THE PREFERRED EMBODIMENTS

Figure 1:
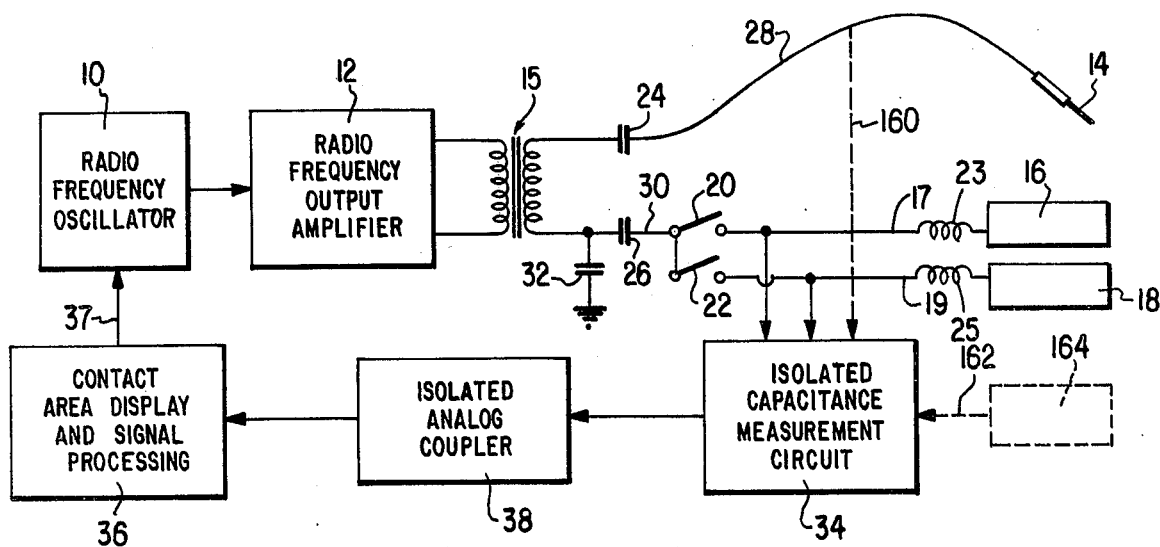
FIG. 1 is a combined schematic and block diagram of illustrative circuitry for effecting a contact area measurement in accordance with the subject invention.

In the drawing, like reference numerals refer to like elements.

Referring to FIG. 1, there is shown a combined schematic and block diagram of illustrative circuitry for effecting a contact area measurement in accordance with this invention. A radio-frequency oscillator 10 is connected to an output amplifier 12, the output of amplifier 12 being applied to active electrode 14 via output transformer 15. The active electrode is placed in contact with a patient (not shown), the patient normally being in complete contact with both of the split electrodes 16 and 18. The current from electrode 14 is thus returned to the low side of transformer 15 via switching contacts 20 and 22 which are normlly open but which are closed during a surgical procedure. A pair of capacitors 24 and 26 are disposed in the leads 28 and 30 to inhibit the circulation of low frequency currents through the patient's body. Capacitor 32 tends to ground the split patient electrodes at radio-frequencies while providing a large impedance to line frequency sink currents.

Connected across the split patient electrodes 16 and 18 is an isolated capacitance measurement circuit 34 which measures the capacitance seen between lines 17 and 19, as will be discussed in more detail hereinafter. The measurement circuit 34 is connected to a contact area display and signal processing circuit 36 via an isolated analog coupler 38. The output of processing circuitry 36 may be used to enable amplifier 12 and to effect the closure of switching contacts 20 and 22 as will now be described with respect to FIG. 2.

Figure 2:
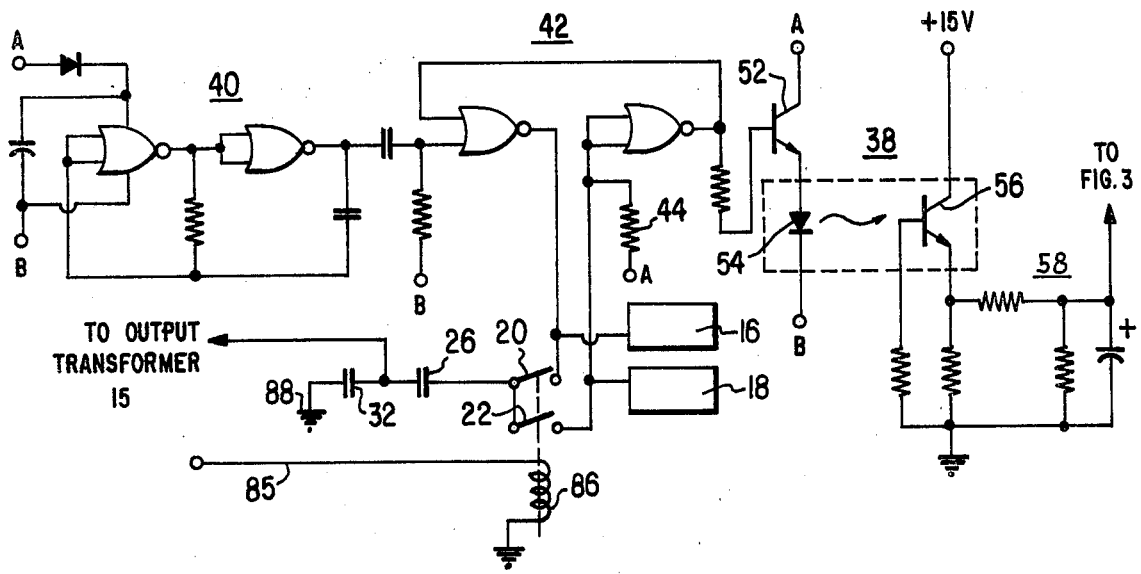
FIG. 2 is a schematic diagram of illustrative circuitry for effecting the capacitance measurement and analog coupling functions of FIG. 1.

FIG. 2 is a schematic diagram of illustrative circuitry of the capacitance measurement circuit 34 and isolated analog coupler 38 of FIG. 1. A CMOS oscillator generally indicated at 40 applies an 1.8 KHz, for example, signal to a single shot multivibrator generally indicated at 42. The time constant of the single shot multivibrator is determined by the resistor 44 and the capacitance associated with split patient electrodes 16 and 18. The nature of this capacitance will be discussed in more detail hereinafter. The resistor 44 is constant. Thus, the width of the square wave output pulses from single shot 42 varies in accordance with the capacitance associated with electrodes 16 and 18. The pulse width modulated output pulses from single shot 42 are transmitted to ground by optical coupler 38. In particular, the pulse width modulated pulses are applied to a light emitting diode 54 via a transistor 52. The modulated light emitted from diode 54 is coupled to a phototransistor 56 and the pulse width modulated information is converted to a proportional DC level by an integrator indicated at 58. The use of pulse width modulation avoids the non-linear characteristics of typical optical couplers.

Figure 3:
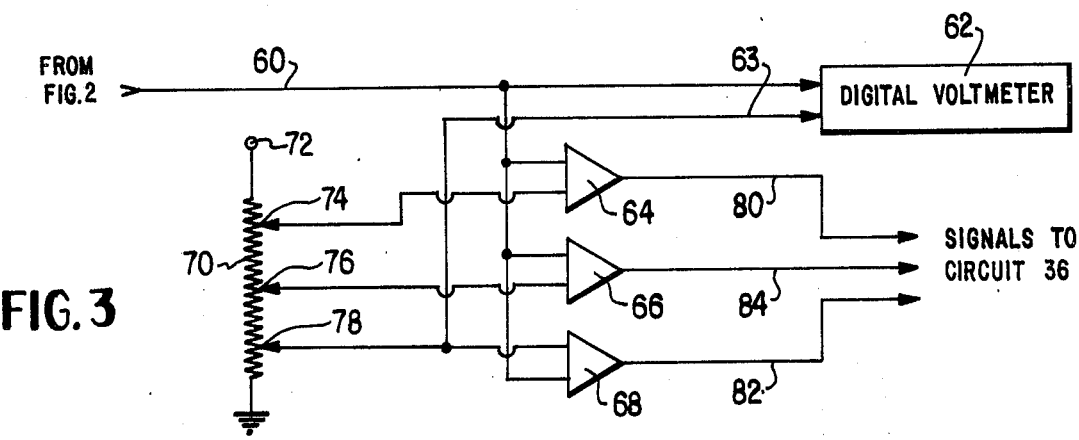
FIG. 3 is a schematic diagram of illustrative circuitry for effecting the contact area display and signal processing function of FIG. 1.

Referring to FIG. 3, there is shown a schematic diagram of an illustrative contact area display and signal processing circuit 36. The proportional DC voltage from integrator 58 is applied to line 60, the voltage being proportional to the measured capacitance or contact area. The signal on line 60 is applied to a digital voltmeter 62 and a plurality of differential amplifiers 64-68. Also applied to voltmeter 62 is a DC offset signal over line 63. The digital voltmeter 62 may be calibrated in terms of contact area to thereby provide a direct reading of measured contact area.

A potentiometer 70 is connected to a regulated, constant reference voltage at terminal 72 and is provided with three taps 74, 76 and 78 which are respectively connected to comparators 64-68. If electrodes 16 and 18 are shorted together, the measured capacitance will be very large and the voltage applied to comparator 64 via line 60 will be substantially greater than the voltage applied from tap 74 thereby indicating that the measured capacitance is substantially greater than the expected capacitance when both electrodes 16 and 18 are in complete contact with the patient's body. Hence, the output signal on line 80 would be applied to processing circuitry 36 where a decision would then be made to disable amplifier 12 over line 37. However, the occurrence of a signal on line 80 of the aforesaid type may also be overridden by processing circuitry 36 if the capacitance measuring circuitry of FIG. 2 is to also be employed with a solid, patient electrode plate.

If the electrodes 16 and 18 and their associated cables 17 and 19 are not connected to the generator, the measured capacitance will be very low and voltage at tap 78 will exceed that on line 60. This condition is detected by comparator 68 and applied to processing circuitry 36 via line 82 to disable amplifier 12.

Assuming the patient is at least in partial contact with the split electrodes 16 and 18, the potential on line 60 will exceed that at tap 76 as long as the contact area between the patient and the split electrodes exceeds a predetermined minimum. This minimum contact area is preferably about 60% of the contact area when the patient is in complete contact with the split electrodes. Thus, as long as the signal on line 60 exceeds that at tap 76, the output signal from comparator 66 on line 84 will be such that processing circuitry 36 will enable amplifier 12. Otherwise, the amplifier is disabled.

The signal employed to enable amplifier 12 may also be applied to line 85 of FIG. 2 to energize a grounding relay 86. Energization of relay 86 closes switching contacts 20 and 22 to permit the current from electrodes 16 and 18 to be returned to the low side of transformer 15. Thus, prior to the surgical procedure (or at predetermined intervals during the procedure), the switching contacts 20 and 22 are opened to permit the capacitive measurement to take place. The measurement circuitry must be isolated from ground 88 and this is effected by opening switches 20 and 22. A further advantage of having switches 20 and 22 open at this time is that it leaves the patient electrode well isolated from ground and thus minimizes line frequency sink currents and source leakages when the generator is not active. Circuitry for isolating the capacitance measuring circuitry of FIG. 2 from a ground, for example, on the patient will now be described with regard to FIG. 4.

Figure 4:
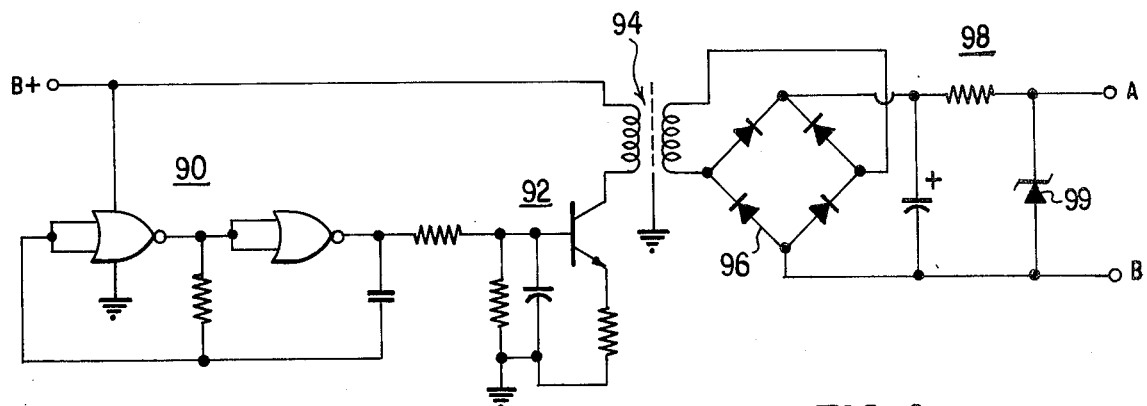
FIG. 4 is a schematic diagram of illustrative circuitry of an isolated power supply for the capacitance measurement circuitry of FIG. 1.

Referring to FIG. 4, there is shown a schematic diagram of an illustrative isolated power supply for the capacitance measuring circuit 34 and the isolated analog coupler 38 of FIGS. 1 and 2. An oscillator generally indicated at 90 generates a 150 KHz signal which is applied to an amplifier indicated at 92. The oscillator 90 and amplifier 92 are chassis ground referenced. The use of a 150 KHz signal is advantageous in that any AC leakage which is inadvertently coupled to the patient plate is at too high a frequency to stimulate muscles or nerves and/or to interfere with ECG patient monitors. The output of amplifier 92 is coupled via an isolation transformer 94 to a diode bridge 96 where it is full wave rectified and then filtered by a filter circuit indicated at 98 and regulated by zener diode 99. The output terminals A and B of filter 98 supply an isolated DC voltage of typically 12 volts to the terminals A and B shown in FIG. 2. Thus, oscillator 40, single shot 42 and light emitting diode 54 are isolated from ground. Thus, the capacitance measurement across plates 16 and 18 is substantially unaffected if the patient happens to be grounded. If the foregoing circuitry were grounded it would be greatly affected by any ground on the patient.

Figure 5:
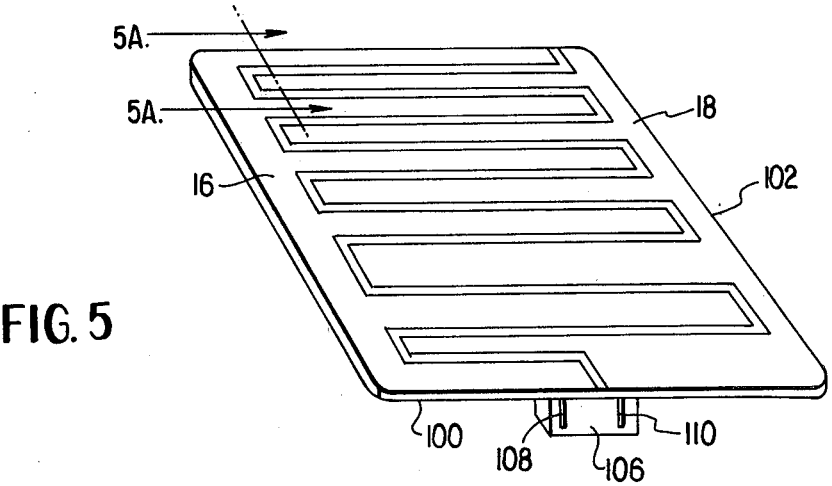
FIG. 5 is a diagrammatic, perspective view of an illustrative insulated, interdigitated split patient electrode in accordance with this invention.
Figure 5A:
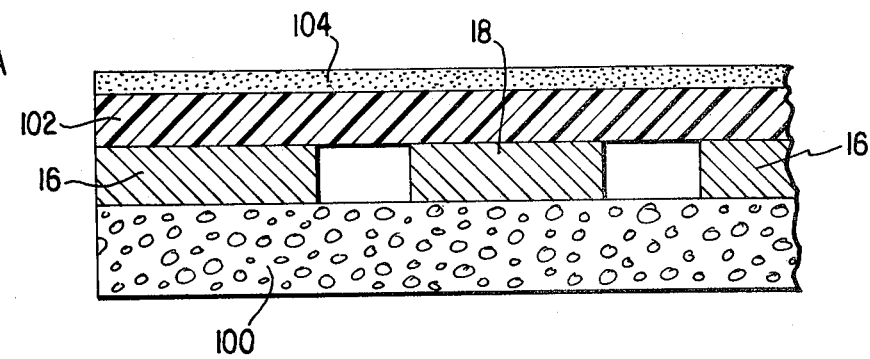
FIG. 5A is a partial cross-sectional view taken on the line 5A—5A of FIG. 5.

Referring to FIG. 5, there is shown a perspective, diagrammatic view of a capacitive, split patient electrode in accordance with this invention, where FIG. 5A is a partial cross-sectional view taken on the line 5A—5A of FIG. 5. A foam backing pad 100 has disposed thereon a pair of interdigitated foil electrodes 16 and 18, the interdigitation enhancing the overlap of the electrodes. Disposed on the electrodes is a dielectric insulating layer 102 which in turn is provided with an adhesive coating 104. A two conductor connector 106 is provided at the underside of backing pad 100. The connector includes prongs 108 and 110 which respectively engage electrodes 16 and 18 and which are respectively connected to wires 17 and 19. Dielectric layer 102 should be thick enough to prevent dielectric breakdown if contacted by the activated active electrode. Thus, the dielectric layer should typically be able to withstand about 5,000 volts. A layer of Mylar at least 0.005 inches thick would be satisfactory.

The capacitive split patient electrode of FIG. 5 is particularly suitable for facilitating the capacitive measurement effected by the circuitry of FIG. 2. Although there is no intent to be limited to a particular theory of operation, it is known the patient's body is a conductor of electricity and therefore, by measuring the series capacitance from split plate 16 to the skin and from the skin to plate 18, a good measurement of the minimum contact area with the skin can be obtained. Also a determination can be made when the split electrodes have been perfectly applied.

A difficulty with a capacitive patient electrode is that the dielectric insulating layer 102 must be fairly thick to prevent breakdown by the high voltage available from the generator. If, as stated above, a Mylar layer at least 0.005 inches thick is employed, the insulation is adequate, but the plate must be quite large to prevent potentially dangerous voltages from occurring between the cable and the patient's skin. This is especially important if the patient side of the generator output circuit is ground referenced. If the generator is well isolated, it is not as important. A typical patient return electrode of the "stick-on" design is relatively small—that is, about 7 by 9 inches. An insulating layer of 0.005" Mylar plus adhesive on a foil electrode of this size yields a capacitance of about 4000pf to skin at radio frequencies for the capacitive split electrode of FIG. 5. If the voltage between the patient's body and ground is to be kept below 30 volts RMS, for example, the current will be limited to about 0.57 amperes at 500KHz. This is adequate for cutting or fulguration, but it is not adequate for desiccation. For desiccation a current of at least 1 ampere RMS is needed so higher frequencies must be used.

Although the total capacitance at 500KHz between the capacitive electrode of FIG. 5 and the skin is about 4000 pf in the example given above, the capacitance between each half of the electrode and the skin is half of that. Since the two halves are measured in series, the capacitance measurement circuitry of FIG. 2 sees about one fourth of the capacitance which is available for conducting radio frequency current across to the patient's skin. If the insulated return electrode is completely applied to a sheet of metal, the expected measurement of about ¼ the total RF capacitance is seen. However, if the return electrode is applied to skin, and the capacitance measurement is done at 1.8KHz, the capacitance is almost twice as high as one obtains if the electrode were fixed to a metal plate. The reason for this paradox seems to be that the body is not an ohmic conductor like a sheet of metal. Instead, much of the conduction is due to ions moving within the tissue cells and, since these ions are not as free to move as electrons in metal, the steady state conduction through tissue or any electrolytic solution is not achieved instantly, but is achieved slowly. This "slowness" makes the charge on the skin side of the capacitance gather more slowly and thus the rate of change of voltage and therefore the apparent capacitance, seems higher. This affect is quite apparent at low frequencies, below 100KHz, but is much less noticeable at radio frequencies. Preferably, the mesurement should be made at a frequency no greater than 3KHz but the measurement current should be no greater than that which would effect neuromuscular stimulation, the measurement being made at 1.8KHz in the circuitry of FIG. 2.

The foregoing phenomenon allows detection of the difference between fixing the return electrode to metal and fixing the electrode to a patient. Thus, even if the return electrode were perfectly applied to, say the metal case of the generator, the capacitance would only be about half aand the safety circuit would not permit the generator to operate. Thus, if the return electrode falls off the patient and comes in contact with ground, it will always appear as insufficient contact area and the safety circuit can shut off the generator.

In summary, some of the advantages of the insulated split electrode of FIG. 5 are as follows:

(1) The patient contact area is actually measured and insufficient contact area can be used to shut off the generator.
(2) This system can discriminate between contact with the tissue and metal. Thus, the system can detect when the return electrode is contacting ground instead of human tissue.
(3) No electrode gel is required. This makes the product cheaper, easier to build, easier to store and easier to apply.
(4) If the split patient electrode becomes shorted, or the system is used with a conventional patient plate, this appears as an extremely high capacitance and thus can be discriminated from a split plate which is in perfect contact with a patient. Since this information is available, the generator can be shut down or flash a warning, as discussed hereinbefore with respect to FIG. 3.
(5) If no patient electrode and cable is plugged into the generator, this appears as an extremely low capacitance and is distinctly different from having the electrode and cable plugged in, but not touching anything. Thus, not having any electrode attached can be detected much like the prior art two wire patient alarm sentry and this situation can shut down the generator.

There are also certain limitations of the insulated split electrode, these being (1) if the foil electrodes are not interdigitated the system can only measure the minimum contact area, since the circuit has no way of knowing whether the capacitance is being limited by the contact area of just one side or both sides and (2) the current which can pass through an insulated plate is limited by the permissible voltage which can occur between the patient cable and the patient's body. This voltage can be made smaller by increasing the generator frequency, but this has other drawbacks such as loss of RF isolation, and the need for heavier insulation on the active cable.

One of the difficulties encountered with a high frequency, grounded generator is that the inductance of the cable connecting the patient electrode to the generator is significant and the voltage drop across this inductance can cause currents to seek other paths to ground via current division. These other current paths could be at small, grounded contact points on the patient's skin and are a threat to the patient. The inductance of a 10 foot cable is about three microhenries. At 2MHz one ampere of current flowing through this inductance can generate a voltage of about 40 volts. In contrast, the impedance of the insulated split patient plate of FIG. 5 drops with frequency and thus the patient cable and the split capacitive electrode comprise a series resonance L-C circuit. With a 4000 pf electrode and a typical ten foot, two-wire cable, the resonance occurs at about 2MHz. Experiments have shown that the Q of this resonance point is such that a pad which is not perfectly applied, say only 80% contact, still has an acceptably low impedance to ground.

The return fault ground monitor described in copending U.S. application Ser. No. 721,821, filed Sep. 9, 1976 by D. Newton, et al. works well with the foregoing resonant system because return fault circuit measures ground currents which are a threat to the patient. If the pad is misapplied, but not necessarily dangerous, the extra voltage to ground will cause currents to flow to ground and these will be detected by the return fault monitor. On the other hand, if there are no such paths to ground, no ground currents will flow and the return fault system will not detect a fault since there is no actual threat to the patient.

It is also possible to put extra inductors (for example, inductors 23 and 25 of FIG. 1) in each lead of the patient cable and make the same capacitive plate resonate at lower operating frequencies. In experiments at 750KHz the Q of such a system is much higher and thus the patient plate application becomes quite critical. That is, if the capacitive electrode lacks a few percent of being perfectly applied, it will have a very high impedance. On the other hand, if it is perfectly applied, the total impedance between the patient's body and ground can be much lower than can be achieved with a conventional plate and a simple 10 foot cable. This situation makes current division much less likely. Thus the inconvenience of the more critical patient electrode application is partially offset by the diminished likelihood of the return fault circuit being triggered.

A gelled embodiment of a split patient plate is also possible. Thus a patient plate with the two halves insulated from each other is provided. A very thin layer of gel is applied to the plate and this in turn is applied to the patient's skin. This system is workable but appears to have two major limitations. First, it can only be placed under the patient or, at best, it could be taped onto the patient. Second, the gel layer must be very thin in order not to short out the measurement. Moreover, the gel layer, no matter how thin, will degrade the accuracy of the contact area measurement.

Figure 6:
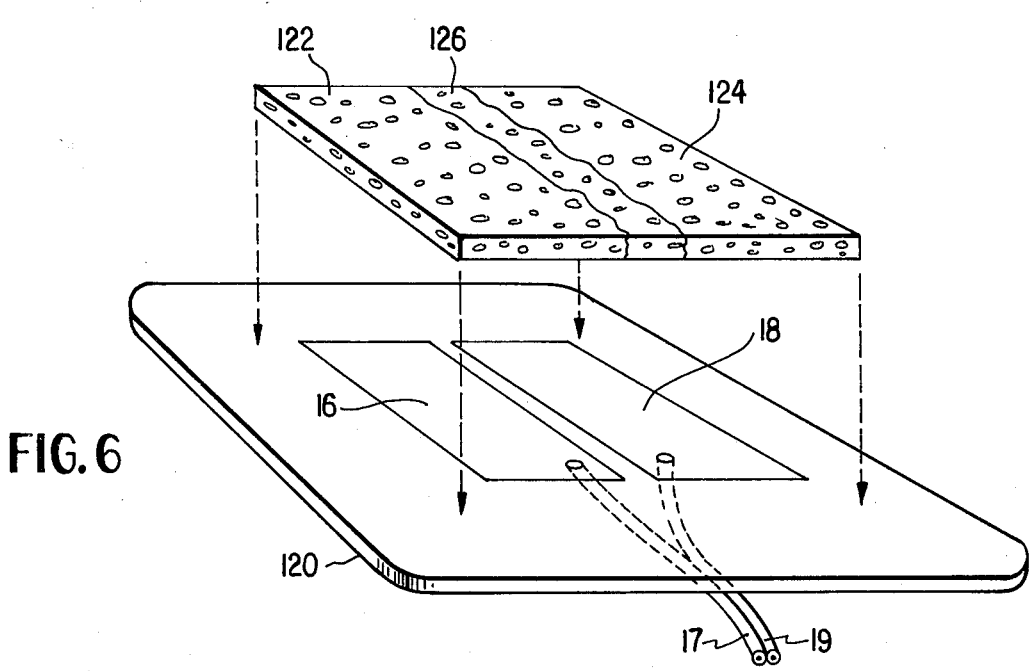
FIG. 6 is a perspective, exploded, diagrammatic view of an illustrative gelled split patient electrode in accordance with this invention.

Referring now to FIG. 6 there is shown an illustrative embodiment of a preferred gelled split patient electrode. A foam backing pad 120 has disposed thereon foil electrodes 16 and 18. An adhesive surface may be provided on pad 120. Respectively disposed over electrode 16 and 18 are layers 122 and 124 of a conventional electroconductive water-based gel. Disposed between layers 122 and 124 is an electrically insulating strip 126 comprised of petroleum jelly or the like. Respectively connected to electrodes 16 and 18 are cables 17 and 19.

Even though there is no dielectric insulating layer corresponding to layer 102 of FIG. 5, the gel contact with the skin still makes a large apparent capacitance, especially at low frequencies. The apparent capacitance in this case appears to be another way of viewing the polarization of an electrolyte when DC is passed through it. When DC voltage is applied to an electrolyte, high levels of current first flow which quickly drop off to a steady state value which represents DC electrolysis of the solution. This drop in current and rise in voltage can be considered capacitance and can be measured with the measuring circuit of FIG. 2. In this case the split gelled patient plate (4"×6") makes a capacitance of about 8 microfarads as seen across the split plate.

Advantages of the gelled split return electrode are (1) the voltage between the patient cable and the patient's body is kept low, even at high current levels and (2) all the advantages previously listed for the insulated split electrode (except those relating to the absence of gel and ease of construction and storage) also apply to the gelled split electrode. Limitations of the gelled split return electrode are (1) it is relatively complex and expensive to fabricate, (2) it has the same storage limitations as other gelled pads, and (3) interdigitation of the split electrodes is not practical.

Figure 7:
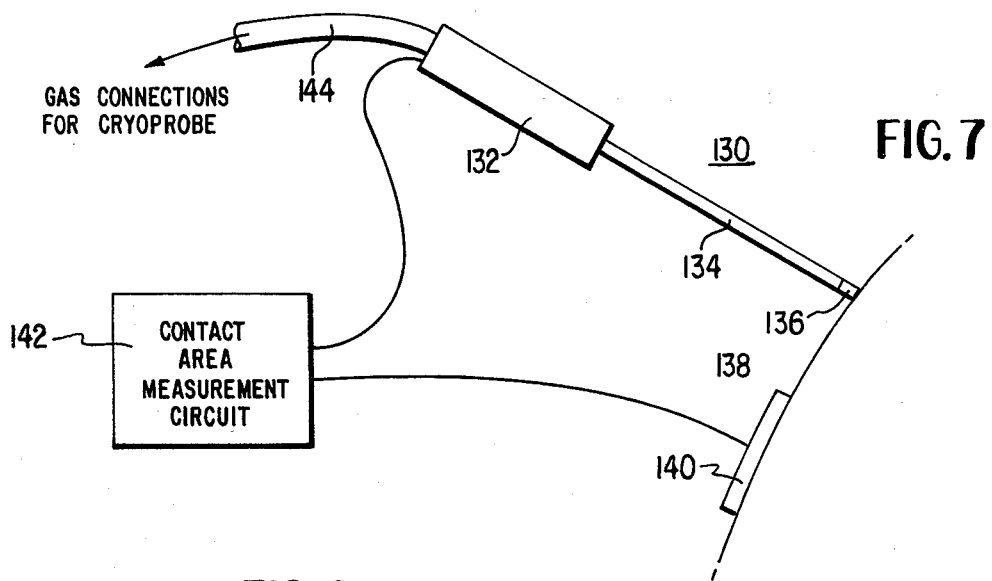
FIG. 7 is a diagrammatic view of an illustrative cryosurgical instrument together with circuitry for measuring the effective contact area of the cryoprobe tip with respect to the patient tissue.

Referring to FIG. 7, there is disclosed an illustrative embodiment of apparatus and circuitry for optimizing the initial conditions for a cryosurgical procedure and for monitoring the results thereof. The cryosurgical instrument or cryoprobe is diagrammatically indicated at 130 and includes handle 132, shank 134 and tip 136 which engages tissue 138. Also disposed on the tissue is a monitor electrode 140 having an adhesive surface for facilitating adhesion thereto. The contact area of the cryoprobe tip 136 with respect to tissue 138 is measured by contact area measurement circuit 142. Gas connections 144 for the cryoprobe are indicated at 144.

In cryosurgery, the effectiveness of the freeze is greatly affected by the thermal conductivity of any barrier between the metal probe and the tissue. For example, dry skin makes a good thermal insulator. By wetting the skin, the probe tip becomes tightly coupled to the tissue and the heat transfer is maximum. However, the skin can be relatively thick and it takes a while for the water to soak into it completely, as evidenced by a slowly rising capacitance reading. In this application, therefore, it is assumed that per unit area, electrical conductivity is proportional to thermal conductivity and this appears to be true.

Area measurement, therefore, is useful for establishing the initial conditions before starting a cryo treatment. Contact area measurement is also useful for monitoring the results of the cryo treatment. During the treatment, the tissue surrounding the probe tip is frozen into an ice ball and the ice becomes electrically inert. Its DC resistance rises above 200 megaohms and the "battery" activity or DC offset voltage drops to zero. Similary, the capacitance reading drops to zero. In the cryo system disclosed in co-pending U.S. application Ser. No. 824,174, filed by R. Mitchiner on Aug. 12, 1977, the probe is actively heated following the freeze to enhance the necrotic effect and to facilitate the removal of the probe from the tissue. It has been observed that the tissue after freezing seems to be just about the same as it was before it was frozen, but the diameter of the ice ball formed is proportional to the length of time that it takes for the probe heater to thaw an electrical pathway through the ice. Therefore, by timing how long it takes for the capacitance measurement to return, a good measurement of how large the ice ball was can be obtained.

By putting all the foregoing information together, a uniform and effective freeze can be obtained.

Figure 8:
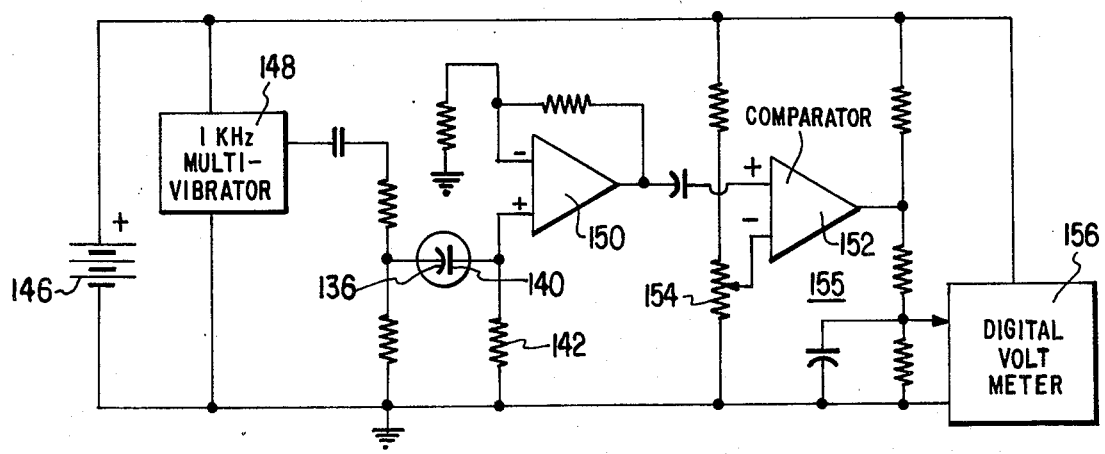
FIG. 8 is a schematic diagram of illustrative circuitry for effecting the contact area measurement function of FIG. 7.

Referring to FIG. 8, there is shown an illustrative schematic diagram of the contact area measurement circuit 142 of FIG. 7. An isolated power source 146 is employed, the power source of FIG. 4 being suitable for this purpose. A one KHz free-running multivibrator 148 generates a 15 millivolt AC square wave which passes through cryoprobe 136 and monitor electrode 140 through a fixed resistance 142. Since resistance 142 is fixed, the current which returns from the patient is a differentiated square wave, the width of which is proportional to the measured capacitance. In particular, since the differentiator is somewhat imperfect a decaying waveform is produced which, after one time constant, for example, will have a width proportional to the capacitance.

The current which passes through the patient is attenuated until it is well under 10 microamperes and is no possible threat of fibrillation or sensation. After the square wave of multivibrator 148 is differentiated, it is amplified by operational amplifier 150 and compared with a fixed reference level at comparator 152, the fixed reference level having been obtained from potentiometer 154. The comparator produces square pulses which have a duration proportional to the measured capacitance. These pulses are integrated at integrator 155 to obtain a DC level proportional to the capacitance. The DC level is then applied to a digital voltmeter 156, for example, which may be calibrated in terms of measured contact area.

In some electrosurgical procedures it is also desirable to know the area of active electrode which is in contact with the tissue, before setting the generator power level or activating the generator. Thus, referring to FIG. 1, there is shown by dotted lines 160 and 162 how the measurement circuit 34 would be connected across active electrode 14 and a unitary patient plate 164 although it is to be understood split patient electrodes 16 and 18 could also be employed.

In the removal of polyps from the gastrointestinal tract, a wire snare is looped around the polyp. An electrosurgical current is passed from the snare to the polyp for the purposes of severing it and achieving hemostasis. If the surgeon intends to cut electrosurgically without desiccation, then he needs to enclose the polyp with the snare as loosely as possible. If he intends to desiccate without any cutting effect, then he needs to grasp it firmly. Since the procedure is generally done through an endoscope, the surgeon's view of the polyp is very restricted and he has no way of knowing whether the snare wire is touching the polyp on the far side of the polyp stalk.

Sphincterectomy of the Papilla of Vater to relieve a stenotic common bile duct in the duodenum is another possible application for this contact area measurement. In sphincterectomy a thin wire cutting electrode mounted on the side of a plastic catheter is inserted into the sphincter. Using a blended electrosurgical current the sphincter is cut on one side by the wire and, like polypectomy, it is desirable to know how much of the wire is in firm contact with the tissue before starting the cut and how far the probe has been inserted into the duct.

In experiments with active electrode contact measurement, the same circuit as used for the patient electrode measurement was employed—that is, the circuitry of FIG. 2. It was found it was practical to make this measurement and calibrate it in terms of millimeters of wire in contact with tissue. A large, gelled, solid patient electrode served as the other half of the measurement circuit. Since its contact area was much larger than that of the wire electrode, the capacitance seen was proportional to the area of the wire and not the large, gelled electrode. The foregoing also applied to the cryoprobe contact area measurement of FIG. 7 where the cryoprobe contact area is much smaller than that of monitor electrode 140.

In summary, features provided by this invention are as follows:

(1) tissue contact area measurement by capacitance measurement with a split patient electrode. (A bipolar measurement.);

(2) the use of a low frequency capacitance measurement signal to differentiate between tissue and metal;

(3) contact area measurement using the principle that the polarization of an electrolytic solution like tissue can be thought of as a capacitor at low frequencies;

(4) contact area measurement using the "monopolar" approach where only one of the two electrodes is the area to be measured;

(5) application of tissue area contact measurement to electrosurgical patient electrodes, electrosurgical active electrodes, cryosurgery, diffibrillator paddles, and diathermy;

(6) the insulated split plate of FIG. 5;

(7) the resonant patient electrode using an insulated patient plate;

(8) adding inductance to tune the patient cable to a resonance with the generator frequency;

(9) the split gelled patient electrode design of FIG. 6;

(10) isolation of the measurement circuit of FIG. 2 so that the patient's body may be grounded;

(11) use of a high frequency isolated power supply as in FIG. 4 so that leakage current to the patient plate (a) will be above the frequency sensitivity of an ECG monitor and (b) cannot stimulate muscles and nerves;

(12) relay coupling to the patient electrode so that 60 Hz active and sink leakages are insignificant even though the generator is grounded at RF frequencies during activation;

(13) use of either of the electrosurgical split patient electrodes of FIGS. 5 and 6 with any ground current monitoring system; and

(14) use of a resonant patient electrode system with a ground current measuring patient plate safety system.

What is claimed is:

1. Patient contact area measurement apparatus for use with an electrosurgical generator comprising a first electroconductive contact element adapted for contact with a patient;

a second electroconductive contact element separated from said first contact element and also adapted for contact with said patient;

means for directly measuring the capacitance between said first and second electroconductive contact elements to thereby measure the area of contact of said patient with respect to said contact elements;

an electrosurgical generator;

an active electrode connected to said generator;

a split patient electrode connected to said generator, said split electrode comprising said first and second electroconductive contact elements; and said capacitance measuring means including means for detecting whether the measured contact area of said patient with respect to said split electrode exceeds a predetermined value corresponding to safe operation of the electrosurgical generator.

2. Apparatus as in claim 1 where said capacitance measurement means includes means for applying a signal between the said first and second electroconductive contact elements, the amplitude of said signal being sufficiently low to avoid neuromuscular stimulation of said patient.

3. Apparatus as in claim 1 where said capacitance measurement means is isolated from ground to thereby avoid any undesirable effect on the contact area measurement due to grounding of said patient.

4. Patient contact area measurement circuitry for use with electrosurgical equipment comprising
   an electrosurgical generator;
   an active electrode connected to said generator;
   a split patient electrode connected to said generator, said split electrode comprising a first electrode separated from a second electrode where both electrodes are adapted for contact with a patient; and
   means for directly measuring the capacitance between said first and second electrodes to thereby measure the contact area of said patient with said split electrode, said capacitance measuring means including means for detecting whether the measured contact area exceeds a predetermind value corresponding to safe operation of the electrosurgical equipment.

5. Circuitry as in claim 4 where said capacitance measuring means includes means for applying a signal between the said first and second electrodes, the amplitude of said signal being sufficiently low to avoid neuromuscular stimulation of said patient.

6. Circuitry as in claim 4 where each of said first and second electrodes includes a dielectric layer of electrically insulating material disposed thereon, each of said dielectric layers being adapted to contact said patient.

7. Circuitry as in claim 6 including a patient cable connected between said split patient electrode and said generator, the capacitance of said split patient electrode and the inductance of said cable forming a series LC circuit which resonates at approximately the operating frequency of said generator.

8. Circuitry as in claim 6 where the frequency of the said signal applied to said electrodes is sufficiently low to enable discrimination between said patient contacting the electrodes and a metallic object contacting the electrodes.

9. Circuitry as in claim 4 including a patient cable connected between said split patient electrode and said generator and an inductor connected in series with said cable, the capacitance of said split patient electrode and the inductance of said cable and said inductor forming a series LC circuit which resonates at approximately the operating frequency of said generator.

10. Circuitry as in claim 4 where said capacitance measuring means is isolated from ground to thereby avoid any undesirable effect on the capacitance measurement due to grounding of said patient.

11. Circuitry for use with electrosurgical equipment comprising
    an electrosurgical generator;
    an active electrode connected to said generator;
    a patient electrode connected to said generator, the area of said patient electrode adapted for contact with a patient being substantially greater than the area of the active electrode adapted for contact with the patient; and
    capacitance measuring means for measuring the capacitance between said active and patient electrodes whereby when both said active and patient electrodes are in contact with the patient, the area of contact of the active electrode will be measured due to the substantially greater contact area of the patient electrode with the patient.

12. An electrosurgical generator for use with a patient comprising
    electrical power generating means;
    an output circuit connected to said electrical power generating means, said output circuit including (a) an active lead and an active electrode connected thereto and (b) a patient lead and a patient electrode connected thereto where said patient electrode includes at least one electroconductive substrate having a dielectric layer of electro-insulative material disposed thereon; and
    an inductor disposed in series with said patient lead so that said patient lead, said inductor and said patient electrode comprise a series LC circuit which resonates approximately at the fundamental frequency of operation of said electrical power generating means.

13. Patient contact area measurement apparatus for use with an electrosurgical apparatus comprising
    a first electroconductive contact element adapted for contact with a patient;
    a second electroconductive contact element separated from said first contact element and also adapted for contact with said patient;
    means for directly measuring the capacitance between said first and second electroconductive contact elements to thereby measure the area of contact of said patient with respect to said contact elements;
    an electrosurgical generator;
    an active electrode connected to said generator comprising said first electroconductive contact element;
    a patient electrode connected to said generator comprising said second electroconductive contact element, said patient electrode having an area adapted for contact with said patient substantially greater than that of said active electrode; and
    said capacitance measuring means measuring the contact area of said active electrode with respect to said patient.

14. Apparatus as in claim 13 where said capacitance measurement means includes means for applying a signal between the said first and second electroconductive contact elements, the amplitude of said signal being sufficiently low to avoid neuromuscular stimulation of said patient.

15. Apparatus as in claim 13 where said capacitance measurement means is isolated from ground to thereby avoid any undesirable effect on the contact area measurement due to grounding of said patient.

* * * * *